(12) United States Patent
Chassot et al.

(10) Patent No.: US 6,849,097 B2
(45) Date of Patent: Feb. 1, 2005

(54) N-HETEROARYLMETHYL-P-PHNYLENDIAMINE DERIVATIVES AND COMPOUNDS CONTAINING OXIDATIONCOLORING AGENTS

(75) Inventors: Laurent Chassot, La Chapellenie (CH); Hans-Juergen Braun, Ueberstorf (CH)

(73) Assignee: Wella Aktiengesellschaft, Darmstadt (DE)

( * ) Notice: Subject to any disclaimer, the term of this patent is extended or adjusted under 35 U.S.C. 154(b) by 231 days.

(21) Appl. No.: 10/111,464
(22) PCT Filed: Mar. 14, 2001
(86) PCT No.: PCT/EP01/02840
§ 371 (c)(1),
(2), (4) Date: Apr. 23, 2002
(87) PCT Pub. No.: WO02/18365
PCT Pub. Date: Mar. 7, 2002

(65) Prior Publication Data
US 2003/0070240 A1 Apr. 17, 2003

(30) Foreign Application Priority Data
Aug. 31, 2000 (DE) .......................................... 100 42 786

(51) Int. Cl.$^7$ ................................................. A61K 7/13
(52) U.S. Cl. ....................... 8/405; 6/406; 6/410; 6/421; 6/459; 6/463; 548/400; 549/29
(58) Field of Search ............................ 8/405, 406, 410, 8/421, 459, 463; 548/400; 549/29

(56) References Cited
U.S. PATENT DOCUMENTS
5,182,941 A 2/1993 Pan .............................. 73/40
5,540,738 A * 7/1996 Chan et al. .................... 8/406
6,042,620 A 3/2000 Braun ............................ 8/410

FOREIGN PATENT DOCUMENTS
DE 41 10 995 A 10/1992
EP 0 984 007 A 3/2000

* cited by examiner

Primary Examiner—Margaret Einsmann
Assistant Examiner—Eisa Elhilo
(74) Attorney, Agent, or Firm—Michael J. Striker

(57) ABSTRACT

The new N-heteroarylmethyl-p-phenylenediamine derivatives have the general formula (I), Oxidation hair dyeing agents are described based on a combination of developing and coupling substance, which contain at least one N-heteroarylmethyl-phenylenediamine derivative of the formula (I), or a physiologically tolerated salt thereof.

8 Claims, No Drawings

N-HETEROARYLMETHYL-P-PHNYLENDIAMINE DERIVATIVES AND COMPOUNDS CONTAINING OXIDATIONCOLORING AGENTS

The invention relates to new N-heteroarylmethyl-p-phenylenediamine derivatives as well as to agents, containing these compounds, for the oxidative dyeing of keratin fibers.

In the field of dyeing keratin fibers, especially dyeing hair, oxidation dyes have gained a major importance. The dyeing comes about here by the reaction between certain developing substances and certain coupling substances in the presence of suitable oxidizing agents. As developing substances, especially 2,5-diaminotolueme, 2,5-diaminophenylethyl alcohol, p-aminophenol and 1,4-diaminobenzyene are used and, as coupling substances, resorcinol, 4-chlororesorcinol, 1-napthol, 3-aminophenol and derivates of m-phenylenediamine are named as examples. Aside from dyeing to the desired intensity, oxidation dyes, which are used to dye human hair, must meet numerous additional requirements. For example, the dyes must be toxicologically and dermatologically safe and the dyeings achieved must have good light stability, permanent waving stability, acid resistance and crocking fastness. In any case, such dyeings must be stable for a period of at least 4 to 6 weeks without the action of light, rubbing and chemical agents. In addition, it must be possible to produce a wide range of different color nuances by combining suitable developing and coupling substances.

The U.S. Pat. No. 5,540,738 discloses oxidation hair dyeing agents, which contain, for example, N-furfuryl-p-phenylenediamine as well as an iodide. However these dyeing agents are not satisfactory from every point of view and, in particular, a satisfactory dyeing result cannot be achieved without the addition of iodide.

There was, therefore, a continuing urgent need for new dye precursors for oxidation dyeing agents, which enable keratin fibers to be dyed intensively even without the addition of iodide.

It has now been found that intensive brown, blue and red color nuances are obtained when N-heteroarylmethyl-p-phenylenediamine derivatives of the general formula (I) are coupled with conventional coupling compounds.

The object of the present invention therefore are N-heteroarylmethyl-p-phenylenediamine derivatives of the general formula (I) or their physiologically tolerated, water-soluble salts,

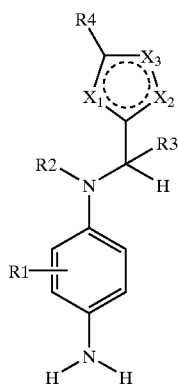

(I)

wherein
X1 is sulfur, nitrogen, C—R6 or N—R5,
X2 is sulfur, nitrogen, C—R6 or N—R5,
X3 is sulfur, nitrogen, oxygen, C—R6 or N—R5,
R1 is hydrogen, a $C_1$–$C_4$ alkyl group or a $C_1$–$C_4$ hydroxyalkyl group,
R2, R3 may be the same or different and, independently of one another are hydrogen or a $C_1$–$C_6$ alkyl group,
R4, R6 may be the same or different and, independently of one another, are hydrogen, a halogen atom, a cyano group, a $C_1$–$C_4$ alkoxy group, a $C_1$–$C_6$ alkyl group, a $C_1$–$C_4$ alkylthioether group, a mercapto group, a nitro group, an amino group, a $C_1$–$C_4$ alkylamino group, a di($C_1$–$C_4$) alkylamino group, a di($C_1$–$C_4$ hydroxyalkyl) amino group, a $C_1$–$C_4$ hydroxyalkylamino group, a trifluoromethane group, a —C(O)CH$_3$— group, a —C(O)CF$_3$— group, an —Si(CH$_3$)$_3$— group, a $C_1$–$C_4$ hydroxyalkyl group or a $C_1$–$C_4$ dihydroxyalkyl group and
R5 is hydrogen, a $C_1$–$C_6$ alkyl group, a $C_1$–$C_4$ hydroxyalkyl group, a phenyl group or an acetyl group,
at least one and not more than two of the X1 to X3 groups being C—R6 and not more than one of the X1 to X3 groups being sulfur, oxygen or N—R5.

The following, for example, may be named as suitable, inventive compounds of formula (I):
N-thiophene-3-ylmethyl-1,4-diaminobenzene, N-furan-3-ylmethyl-1,4-diaminobenzene, N-(1H-imidazole-2-ylmethyl)-1,4-diaminobenzene, N-(1H-pyrrole-2-ylmethyl)-1,4-diaminobenzene, N-(N-methyl-pyrrole-2-ylmethyl)-1,4-diaminobenzene, N-thiophene-2-ylmethyl-1,4-diaminobenzene, N-thiazole-2-ylmethyl-1,4-diaminobenzene, N-(5-nitrothiophene-2-ylmethyl)-1,4-diaminobenzene, N-(3-methyl-thiophene-2-ylmethyl)-1,4-diaminobenzene, N-(2-methyl-thiophene-3-ylmethyl)-1,4-diaminobenzene, N-(4-methyl-thiophene-3-ylmethyl)-1,4-diaminobenzene, N-(5-methyl-thiophene-2-ylmethyl)-1,4-diaminobenzene, N-(3-chloro-thiophene-2-ylmethyl)-1,4-diaminobenzene, N-(4-methyl-thiophene-2-ylmethyl)-1,4-diaminobenzene, N-(4-chloro-thiophene-2-ylmethyl)-1,4-diaminobenzene, N-(5-methyl-thiophene-2-ylmethyl)-1,4-diaminobenzene, N-(5-chloro-thiophene-2-ylmethyl)-1,4-diaminobenzene, 2-[(4-amino-phenyl)-thiophene-2-ylmethyl-amino]-ethanol, 2-[(4-amino-phenyl)-1H-imidazole-2-ylmethyl-amino]-ethanol, N-methyl-N-thiophene-3-ylmethyl-1,4-diaminobenzene, N-methyl-N-furan-3-ylmethyl-1,4-diaminobenzene, N-methyl-N-(1H-imidazole-2-ylmethyl)-1,4-diaminobenzene, N1-(1H-imidazole-2-ylmethyl)-1,4-diamino-2-methylbenzene, N4-(1H-imidazole-2-ylmethyl)-1,4-diamino-2-methylbenzene, N1-furan-3-ylmethyl-1,4-diamino-2-methylbenzene, N4-furan-3-ylmethyl-1,4-diamino-2-methylbenzene, N1-thiophene-2-ylmethyl-1,4-diamino-2-methylbenzene, N4-thiophene-2-ylmethyl-1,4-diamino-2-methylbenzene, 2{5-amino-2-[(furan-2-ylmethyl)-amino]-phenyl}-ethanol, 2-{6-amino-3-[(furan-2-ylmethyl)-amino]-phenyl}-ethanol, 2-{5-amino-2-[(thiophene-3-ylmethyl)-amino]-phenyl}-ethanol, 2-{6-amino-3-[(thiophene-3-ylmethyl)-amino]-phenyl}-ethanol, 2-{5-amino-2-[(thiophene-2-ylmethyl)-amino]-phenyl}-ethanol, 2-{6-amino-3-[(thiophene-2-ylmethyl)-amino]-phenyl}-ethanol.

Preferred are compounds of formula (I), in which (i) R1, R2 and R3 or R1, R2, R3 and R4 are hydrogen or (ii) R1, R2 and R3 or R1, R2, R3 and R4 are hydrogen and X1 is sulfur or NH and X2 is nitrogen or C—R6 and X3 is C—R6 or (iii) R1, R2 and R3 or R1, R2, R3, and R4 are hydrogen and X3 is sulfur or oxygen and X1 and X2 are C—R6 or (iv) R1, R2 and R3 or R1, R2, R3 and R4 are hydrogen and X2 is sulfur or oxygen and X1 and X3 are C—R6.

In the sense of the invention, the following are particularly suitable N-heteroarylmethyl-p-phenylenediamine derivatives of formula (I): N-thiophene-3-ylmethyl-1,4-diaminobenzene, N-furan-3-ylmethyl-1,4-diaminobenzene, N-(1H-imidazole-2-ylmethyl)-1,4-diaminobenzene, N-(1H-pyrrole-2-ylmethyl)-1,4-diaminobenzene and N-thiophene-2-ylmethyl-1,4-diaminobenzene or their physiologically tolerated salts.

The compounds of formula (I) can be used as free bases as well as in the form of their physiologically tolerated salts with inorganic or organic acids such as hydrochloric acid, sulfuric acid, phosphoric acid, acetic acid, propionic acid, lactic acid or citric acid.

The inventive N-heteroarylmethyl-p-phenylenediamine derivatives of formula (I) can be synthesized using known methods. The compounds of formula (I) can be synthesized, for example, as follows:

(1) by a reductive alkylation of a substituted benzene of formula (II)

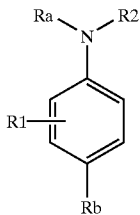

with a heteroaryl compound of formula (III)

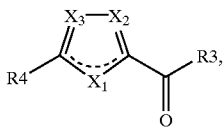

wherein
Rb represents NHRa or $NO_2$,
Ra is a protective group, similar to those described, for example, in the chapter "Protective Groups" in Organic Synthesis, Chapter 7, Wiley Interscience, 1991, X1, X2, X3, R1, R2, R3 and R4 have the meaning given in formula (I) and (2) splitting off the protective group or splitting off the protective group and reducing the nitro group.

The compounds of formula (I) make possible a wide range of different color shades, which extend from blond to brown to purple to violet to blue and to black color shades and are outstandingly suitable for use in dyeing agents for keratin fibers.

Agents for the oxidative dyeing of keratin fibers, such as hair, furs, feathers or wool and, in particular, human hair, on the basis of a combination of developing and coupling substances, which contain at least one N-heteroarylmethyl-p-phenylenediamine derivative of the above formula (I) as developing substance, are a further object of the invention.

The N-heteroarylmethyl-p-phenylenediamine derivative of formula (I) is used in the inventive dyeing agent in an amount of about 0.005 to 20% by weight, an amount of about 0.01 to 5.0% by weight and, in particular, of about 0.1 to 2.5% by weight being especially preferred.

As coupling substances, preferably 2,6-diamino-pyridine, 2-amino-4-[(2-hydroxyethyl)amino]-anisole, 2,4-diamino-1-fluoro-5-methylbenzene, 2,4-diamino-1-methoxy-5-methylbenzene, 2,4-diamino-1-ethoxy-5-methylbenzene, 2,4-diamino-1-(2-hydroxyethoxy)-5-methylbenzene, 2,4-di[(2-hydroxyethyl)amino]-1,5-dimethoxybenzene, 2,3-diamino-6-methoxy-pyridine, 3-amino-6-methoxy-2-(methylamino)-pyridine, 2,6-diamino-3,5-dimethoxy-pyridine, 3,5-diamino-2,6-dimethoxypyridine, 1,3-diaminobenzene, 2,4-diamino-1-(2-hydroxyethoxy)-benzene, 2,4-diamino-1,5-di(2-hydroxyethoxy)-benzene, 1-(2-aminoethoxy)-2,4-diaminobenzene, 2-amino-1-(2-hydroxyethoxy)-4-methylaminobenzene, 2,4-diaminophenoxy-acetic acid, 3-[di(2-hydroxyethyl)amino]-aniline, 4-amino-2-di[(2-hydroxyethyl)amino]-1-ethoxybenzene, 5-methyl-2-(1-methylethyl)-phenol, 3-[(2-hydroxyethyl)amino]-aniline, 3-[(2-amino-ethyl)amino]-aniline, 1,3-di(2,4-diaminophenoxy)-propane, di(2,4-diamino-phenoxy)-methane, 1,3-diamino-2,4-dimethoxybenzene, 2,6-bis(2-hydroxy-ethyl)amino toluene, 4-hydroxyindole, 3-dimethylamino-phenol, 3-diethylamino-phenol, 5-amino-2-methyl-phenol, 5-amino-4-fluoro-2-methyl-phenol, 5-amino-4-methoxy-2-methyl-phenol, 5-amino-4-ethoxy-2-methyl-phenol, 3-amino-2,4-dichlorophenol, 5-amino-2,4-dichlorophenol, 3-amino-2-methyl-phenol, 3-amino-2-chloro-6-methyl-phenol, 3-amino-phenol, 2[(3-hydroxyphenyl)amino]-acetamide, 5-[(2-hydroxyethyl)amino]-2-methyl-phenol, 3-[(2-hydroxyethyl)amino]-phenol, 3-[(2-methoxyethyl)-amino]-phenol, 5-amino-2-ethyl-phenol, 2-(4-amino-2-hydroxyphenoxy)-ethanol, 5-[(3-hydroxypropyl)amino]-2-methyl-phenol, 3-[(2,3-dihydroxy-propyl)amino]-2-methyl-phenol, 3-[(2-hydroxyethyl)amino]-2-methyl-phenol, 2-amino-3-hydroxy-pyridine, 5-amino-4-chloro-2-methyl-phenol, 1-naphthol, 1,5-dihydroxy-naphthalene, 1,7-dihydroxy-naphthalene, 2,3-dihydroxy-naphthalene, 2,7-dihydroxy-naphthalene, 2-methyl-1-naphthol acetate, 1,3-dihydroxybenzene, 1-chloro-2,4-dihydroxybenzene, 2-chloro-1,3-dihydroxybenzene, 1,2-dichloro-3,5-dihydroxy-4-methylbenzene, 1,5-dichloro-2,4-dihydroxybenzene, 1,3-dihydroxy-2-methylbenzene, 3,4-methylenedioxy-phenol, 3,4-methylenedioxy-aniline, 5-[(2-hydroxyethyl)amino]-1,3-benzodioxol, 6-bromo-1-hydroxy-3,4-methylenedioxy-benzene, 3,4-diaminobenzoic acid, 3,4-dihydro-6-hydroxy-1,4(2H)-benzoxazine, 6-amino-3,4-dihydro-1,4(2H)-benzoxazine, 3-methyl-1-phenyl-5-pyrazolone, 5,6-dihydroxy-indole, 5,6-dihydroxy-indoline, 5-hydroxy-indole, 6-hydroxy-indole, 7-hydroxy-indole and 2,3-indolinedione come into consideration.

Although the advantageous properties of the p-diaminobenzene derivatives of formula (I), described here, suggest that these be used alone as developing substance, it is, of course, also possible to use the p-diaminobenzene derivatives of formula (I) together with known developing substances, such as 1,4-diaminobenzene, 2,5-diaminotoluene, 2,5-diaminophenylethylalcohol, 4-aminophenol and its derivatives, such as 4-amino-3-methylphenol, 4,5-diamino-1-(2-hydroxyethyl)-pyrazole or tetraminopyrimidines.

The coupling substances and developing substances may be contained in the inventive dyeing agents in each case individually or in admixture with one another. Preferably, the total amount of coupling substances and developing substances in the inventive dyeing agent (based on the total amount of the dyeing agent) in each case is about 0.005 to 20% by weight, preferably about 0.01 to 5.0% by weight and particularly 0.1 to 2.5% by weight.

The total amount of the combination of developing and coupling substances, contained in the dyeing agent described here, preferably is about 0.01 to 20% by weight, an amount of about 0.02 to 10% by weight and, in particular, an amount of 0.2 to 6% by weight being particularly preferred. The developing and coupling substances generally are used in equimolar amounts. However, it is not disadvantageous if the developing substances are present in a greater or lesser amount, such as in a ratio to the coupling substance of 2:1 to 0.5:1.

Furthermore, the inventive dyeing agent may contain other dye components, such as 6-amino-2-methylphenol and 2-amino-5-methylphenol, as well as conventional direct dyes, for example, triphenylmethane dyes such as 4-[(4'-aminophenyl)-(4'-imino-2",5"-cyclohexadiene-1"-ylidene)-methyl]-2-methylaminobenzene monohydrochloride (C.I. 42 510) and 4-[(4'-amino-3'-methyl-phenyl)-(4"-imino-3"-methyl-2",5"-cyclohexadiene-1"-ylidene)-methyl]-2-methyl-aminobenzene monohydrochloride (C.I. 42 520), aromatic nitro dyes such as 4-(2'hydroxyethyl)amino-nitrotoluene, 2-amino-4,6-dinitrophenol, 2-amino-5-(2'-hydroxyethyl)-amino-nitrobenzene, 2-chloro-6-(ethylamino)-4-nitrophenol, 4-chloro-N-(2-hydroxyethyl)-2-nitroaniline, 5-chloro-2-hydroxy-4-nitroaniline, 2-amino-4-chloro-6-nitrophenol and 1-[(2'-ureidoethyl)amino-4-nitrobenzene azo dyes such as 6-[(4'-aminophenyl)azo]-5-hydroxy-naphthalene-1-disodium sulfonate (C.I. 14 805) and dispersion dyes such as 1,4-diaminoanthraquinone and 1,4,5,8-tetraaminoanthraquinone. The dyeing agents may contain these dye components in an amount of about 0.1 to 4% by weight.

Of course, the coupling and developing substances, as well as the other dye components, provided that they are bases, may also be used in the form of the physiologically tolerated salts with organic or inorganic acids, such as hydrochloric acid or sulfuric acid, or, if they have aromatic OH groups, in the form of the salts of bases, such as alkali phenolates.

Moreover, if the dyeing agents are to be used for dyeing hair, they may also contain further, conventional, cosmetic additives, such as antioxidants like ascorbic acid, thioglycolic acid or sodium sulfite, as well as well as perfume oils, complexing agents, wetting agents, emulsifiers, thickeners and care materials. The inventive dyeing agent may be prepared in the form of a solution, especially an aqueous or aqueous alcoholic solution. However, the especially preferred forms of preparation are a cream, a gel or an emulsion. The composition represents a mixture of dyeing agent components with additives, which are customary for such preparations.

Conventional additives for solutions, creams, emulsions or gels are, for example, solvents such as water, low molecular weight aliphatic alcohols, such as ethanol, propanol or isopropanol, glycerin or glycols such as 1,2-propylene, glycol, furthermore wetting agents or emulsifiers from the classes of anionic, cationic, amphoteric or nonionic surface-active substances such as fatty alcohol sulfates, ethoxylated fatty alcohol sulfates, alkylsulfonates, alkylbenzenesulfonate, alkyltrimethylammonium salts, alkylbetaines, ethoxylated fatty alcohols, ethoxylated nonylphenols, fatty acid alkanolamides and ethoxylated fatty acid esters, furthermore, thickeners such as higher molecular weight fatty alcohols, starch, cellulose derivatives, petrolatum, paraffin oil and fatty acids, as well as care materials, such as cationic resins, lanolin derivates, cholesterol, pantothenic acid and betaine. The components mentioned are used in amounts customary for such purposes, for example, the wetting agents and emulsifiers in concentrations of about 0.5 to 30% by weight, the thickness in an amount of about 0.1 to 25% by weight and the care materials in a concentration of about 0.1 to 5.0% by weight.

The inventive dyeing agent may be weakly acidic, neutral or alkaline, depending upon its composition. In particular, it has a pH of 6.5 to 11.5, the adjustment to a basic pH preferably made with ammonia. However, organic amines, such as monoethanolamine and triethanolamine, or also inorganic bases, such as sodium hydroxide and potassium hydroxide, may also be used. Inorganic or organic acids, such as phosphoric acid, acetic acid, citric acid or tartaric acid come into consideration for adjusting the pH to an acidic value.

For use in oxidative dyeing of hair, the dyeing agents described above are mixed immediately before use with an oxidizing agent and this mixture is applied in an amount, which is sufficient for dyeing the hair, depends upon the fullness of the hair and generally is about 60 to 200 gram.

As oxidizing agent for developing the hair dyeing, mainly hydrogen peroxide or its addition compounds with urea, melamine, sodium borate or sodium carbonate, in the form of a 3% to 12% and preferably 6% aqueous solution, but also oxygen from the air come into consideration. If a 6% hydrogen peroxide solution is used as oxidizing agent, the ratio by weight of hair dyeing agent to oxidizing agent is 5:1 to 1:2 and preferably 1:1. Larger amounts of oxidizing agents are used especially for higher concentrations of dyes in the hair dyeing agent or if it is intended to bleach the hair more strongly at the same time. The mixture is allowed to act for about 10 to 45 minutes and preferably for 30 minutes on the hair at a temperature of 15° to 50° C., after which the hair is rinsed with water and dried. Optionally, at the conclusion of this rinsing, the hair is washed with a shampoo and possibly with a weak organic acid, such as citric acid or tartaric acid. Subsequently, the hair is dried.

The inventive dyeing agents, containing diaminobenzene derivatives of formula (I) as developing substance, make dyeings possible with excellent colorfastness, especially as far as the light fastness, wash fastness and crocking resistance are concerned. With respect to the dyeing properties, the inventive dyeing agents offer a wide range of different color nuances, which depend on the nature and composition of the dye components and extend from blonde to brown to purple to violet to blue and to black. The color shades are distinguished here especially by their color intensity. The very good dyeing properties of the dyeing agents of the present invention are furthermore shown especially by the fact that these agents also enable grayish hair, which has not been pre-damaged chemically, to be dyed without problems and with a good covering power.

The N-heteroarylmethyl-p-phenylenediamine derivatives of formula (I), used in the inventive agents, are readily soluble in water and make possible dyeings with a high color intensity and excellent colorfastness, especially as far as the lightfastness, washfastness and crocking resistance are concerned. They furthermore have an excellent shelf life, especially as a component of the dyeing agents described above.

The following examples are intended to explain the object of the invention in greater detail without limiting it.

EXAMPLES

Example 1

Synthesis of N-Heteroarylmethyl-p-phenylenediamines

The t-butyl ester of N-(4-aminophenyl)-carbamic acid (0.031 g, 0.15 mmoles) and 0.1 mmoles of the appropriate aldehyde are dissolved in 1,2-dichloroethane. Subsequently, 0.1 mL of an acetic acid solution (1 molar in 1,2-dichloroethane) and 0.06 g of NaBH(OAc)$_3$ (0.3 mmoles) are added and the reaction mixture is stirred for 5 to 15 hours at room temperature. At the end of the reaction, the reaction mixture is poured into 10 mL of ethyl acetate and the organic phase is extracted with sodium hydrogen carbonate and then dried with magnesium sulfate. The solvent is distilled off in a rotary evaporator and the residue purified on silica gel with a 9:1 mixture of petroleum ether and ethyl acetate. The product obtained is heated to 50° C. in 4 mL of ethanol and 1.5 mL of a 2.9 molar solution of ethanolic hydrochloric acid. The precipitate is filtered off, washed twice with 1 mL of ethanol and then dried.

a. N-Thiophene-3-ylmethyl-1,4-diaminobenzene Hydrochloride
   Aldehyde used: thiophene-3-carbaldehyde
   Yield: 0.025 g (90% of the theoretical)
   Mass spectrum: MH$^+$ 205(100)

b. N-Furan-3-ylmethyl-1,4-diaminobenzene Hydrochloride
   Aldehyde used: furan-3-carbaldehyde
   Yield: 0.025 g (95% of the theoretical)
   Mass spectrum: MH$^+$ 189(100)

c. N-(1H-imidazole-2-ylmethel)-1,4-diaminobenzene Hydrochloride
   Aldehyde used: imidazole-2-carbaldehyde
   Yield: 0.025 g (83% of the theoretical)
   Mass spectrum: MH$^+$ 189(100)

d. N-Thiophene-2-ylmethyl-1,4-diaminobenzene Hydrochloride
   Aldehyde derivative used: thiophene-2-carbaldehyde
   Yield: 0.025 g (90% of the theoretical)
   Mass spectrum: MH$^+$ 205(100)

e. N-Thiazole-2-ylmethyl-1,4-diaminobenzene Hydrochloride
   Aldehyde derivative used: thiazole-2-carbaldehyde
   Yield: 0.025 g (79% of the theoretical)
   Mass spectrum: MH$^+$ 316(100)

f. N-(Nitro-thiophene-2-ylmethyl)-1,4-diaminobenzene Hydrochloride
   Aldehyde derivative used: 5-nitro-thiophene-2-carbaldehyde
   Yield: 0.025 g (77% of the theoretical)
   Mass spectrum: MH$^+$ 250(60)

Example 2

Synthesis of N1-Heteroarylmethyl-2-methyl-1,4-diaminobenzenes and N4-heteroarylmethyl-2-methyl-1,4-diaminobenzenes A mixture of 0.033 gram (0.15 mmoles) of a mixture of the t-butyl ester of N-(4-amino-2-methylphenyl)carbamic acid and the t-butyl ester of N-4-amino-3-methylphenyl) carbamic acid and 0.10 mmoles of the appropriate aldehyde are dissolved in 1,2-dichloroethane. Subsequently, 0.1 mL of an acetic acid solution (1 molar in 1,2-dichloroethane) and 0.06 g of NaBH(OAc)$_3$ (0.3 mmoles) are added and the reaction mixture is stirred for 5 to 15 hours at room temperature. At the end of the reaction, the reaction mixture is poured into 10 mL of ethyl acetate and the organic phase is extracted with sodium hydrogen carbonate and then dried with magnesium sulfate. The solvent is distilled off in a rotary evaporator and the residue purified on silica gel with a 9:1 mixture of petroleum ether and ethyl acetate. The product obtained is heated to 50° C. in 4 mL of ethanol and 1.5 mL of a 2.9 molar solution of ethanolic hydrochloric acid. The precipitate is filtered off, washed twice with 1 mL of ethanol and then dried.

a. N1-(1H-imidazole-2-ylmethyl)-1,4-diamino-2-methylbenzene Hydrochloride and N4-(1H-imidazole-2-ylmethyl)-1,4-diamino-2-methylbenzene Hydrochloride
   Aldehyde used: imidazole-2-carbaldehyde
   Yield: 0.025 g (40% of the theoretical)
   Mass spectrum: MH$^+$ 203(100)

b. N1-Furan-3-ylmethyl-1,4-diamino-2-methylbenzene hydrochloride and N4-furan-3-ylmethyl-1,4-diamino-2-methylbenzene Hydrochloride
   Aldehyde derivative used: furan-3-carbaldehyde
   Yield: 0.025 g (45% of the theoretical)
   Mass spectrum: MH$^+$ 203(100)

c. N1-Thiophene-2-ylmethyl-1,4-diamino-2-methylbenzene hydrochloride and N4-thiophene-2-ylmethyl-1,4-diamino-2-methylbenzene Hydrochloride
   Aldehyde derivative used: thiophene-2-carbaldehyde
   Yield: 0.025 g (42% of the theoretical)
   Mass spectrum: MH$^+$ 219(100)

Example 3

Synthesis of N1-Heteroarylmethyl-2-(2'-hydroxyethyl)-1,4-diaminobenzenes and N4-heteroarylmethyl-2-(2'-hydroxyethyl)-1,4-diaminobenzenes A mixture of 0.038 gram (0.15 mmoles) of the t-butyl ester of N-(4-amino-2-(2-hydroxyethyl)phenyl)carbamic acid and the t-butyl ester of N-(4-amino-3-(2-hydroxyethyl) phenyl)carbamic acid and 0.10 mmoles of the appropriate aldehyde are dissolved in 1,2-dichloroethane. Subsequently, 0.1 mL of an acetic acid solution (1 molar in 1,2-dichloroethane) and 0.06 g of NaBH(OAc)$_3$ (0.3 mmoles) are added and the reaction mixture is stirred for 5 to 15 hours at room temperature. At the end of the reaction, the reaction mixture is poured into 10 mL of ethyl acetate and the organic phase is extracted with sodium hydrogen carbonate and then dried with magnesium sulfate. The solvent is distilled off in a rotary evaporator and the residue purified on silica gel with a 9:1 mixture of petroleum ether and ethyl acetate. The product obtained is heated to 50° C. in 4 mL of ethanol and 1.5 mL of a 2.9 molar solution of ethanolic hydrochloric acid. The precipitate is filtered off, washed twice with 1 mL of ethanol and then dried.

a. 2-{5-amino-2-[(thiophene-3-ylmethyl)-amino]-phenyl}-ethanol Hydrochloride and 2-{6-amino-3-[(thiophene-3-ylmethyl)-amino]-phenyl}-ethanol Hydrochloride
   Aldehyde derivative used: thiophene-3-carbaldehyde
   Yield: 0.025 g (38% of the theoretical)
   Mass spectrum: MH$^+$ 249(15), [M-thienyl]+152(100)

b. 2-{5-amino-2-[(thiophene-2-ylmethyl)-amino]-phenyl}-ethanol Hydrochloride and 2-{6-amino-3-[(thiophene-2-ylmethyl)-amino]-phenyl}-ethanol Hydrochloride
   Aldehyde derivative used: thiophene-2-carbaldehyde
   Yield: 0.025 g (38% of the theoretical)
   Mass spectrum: MH$^+$ 249(15), [M-thienyl]+152(100)

Examples 4 to 16

Hair Dyeing Agent

Hair dyeing solutions of the following composition are prepared:

| | |
|---|---|
| 1.25 mmole | developing substance of formula (I) of Table 1 |
| 1.25 mmole | coupling substance of Table 1 |
| 1.0 g | potassium oleate (8% aqueous solution) |
| 1.0 g | ammonia (22% aqueous solution) |
| 1.0 g | ethanol |
| 0.3 g | ascorbic acid |
| ad 100.0 g | water |

Immediately before use, 50 g of the above dyeing solution are mixed with 50 g of a 6% aqueous hydrogen peroxide solution. Subsequently, the mixture is applied on bleached hair. After a period of action of 30 minutes at 40° C., the hair is rinsed with water, washed with a conventional, commercial shampoo and dried. The resulting dyeings are summarized in Table 1.

TABLE 1

| Example No. | Developing Substance of Formula (I) | Coupling Substance I. 1,3-dihydroxy-benzene | II. 1,3-diamino-4-(2'-hydroxy-ethoxy)-benzene sulfate | III. 5-amino-2-methyl-phenol | IV. 1-naphthol |
|---|---|---|---|---|---|
| 4. | of Example 1a | brown | dark blue | purple | blue |
| 5. | of Example 1b | brown | dark blue | purple | blue |
| 6. | of Example 1c | dark blond | dark blue | purple | blue |
| 7. | of Example 1d | dark blond | blue | purple | violet |
| 8. | of Example 1e | dark blond | blue | purple | gray |
| 9. | of Example 1f | dark blond | blue | purple | blue |
| 10. | of Example 1g | dark blond | blue | purple | blue |
| 11. | of Example 1h | light brown | gray | red | brown |
| 12 | of Example 2a | medium blond | blue | purple | violet |
| 13. | of Example 2b | medium blond | blue | purple | violet |
| 14. | of Example 2c | light blond | blue | purple | violet |
| 15. | of Example 3a | light blond | blue | purple | blue |
| 16. | of Example 3b | light blond | blue | purple | blue |

Examples 16 to 56

Hair Dye

Hair dyeing solutions of the following composition are prepared:

```
     X g  N-heteroarylmethyl-p-phenylenediamine of formula (I)
          (developing substance E1 to E4 of Table 2)
     U g  Developing substance E8 to E15 of Table 2
     Y g  Coupling substance K11 to K36 of Table 4
     Z g  direct dyes D1 to D3 of Table 3
10.000 g  potassium oleate (8% aqueous solution)
10.000 g  ammonia (22% aqueous solution)
10.000 g  ethanol
 0.300 g  ascorbic acid
ad 100.000 g  water
```

Immediately before use, 30 g of the above dyeing solution is mixed with 30 g of a 6% aqueous hydrogen peroxide solution. Subsequently, the mixture is applied on bleached hair. After a period of action of 30 minutes at 40° C., the hair is rinsed with water, washed with a conventional, commercial shampoo and dried. The resulting dyeings are summarized in Table 5.

Examples 57 to 80

Hair Dyeing Agents

Creamy dye carrier formulations of the following composition are prepared:

```
     X g  N-heteroarylmethyl-p-phenylenediamine of Formula (I)
          (developing substance E1 to E4 of Table 2)
     U g  Developing substance E8 to E15 of Table 2
     Y g  Coupling substance K11 to K36 of Table 4
     Z g  direct dyes D2 of Table 3
  15.0 g  cetyl alcohol
   0.3 g  ascorbic acid
   3.5 g  sodium lauryl alcohol digylcol ether sulfate, 28% aqueous
          solution
   3.0 g  ammonia, 22% aqueous solution
   0.3 g  sodium sulfite, anhydrous
ad 100.0 g  water
```

Immediately before use, 30 g of the above dyeing solution is mixed with 30 g of a 6% aqueous hydrogen peroxide solution. Subsequently, the mixture is applied on bleached hair. After a period of action of 30 minutes, the hair is rinsed with water, washed with a conventional, commercial shampoo and dried. The resulting dyeings are summarized in Table 6.

TABLE 2

| | Developing Substances |
|---|---|
| E1 | N-thiophene-3-ylmethyl-1,4-diaminobenzene hydrochloride |
| E2 | N-furan-3-ylmethyl-1,4-diaminobenzene hydrochloride |
| E3 | N-(1H-imidazole-2-ylmethyl)-1,4-diaminobenzene hydrochloride |
| E4 | N-thiophene-2-ylmethyl-1,4-diaminobenzene hydrochloride |
| E8 | 1,4-diaminobenzene |
| E9 | 2,5-diamino-phenylethanol sulfate |
| E10 | 3-methyl-4-amino-phenol |
| E11 | 4-amino-2-aminomethyl-phenol dihydrochloride |
| E12 | 4-amino-phenol |
| E13 | N,N-bis(2'-hydroxyethyl)-p-phenylenediamine sulfate |
| E14 | 4,5-diamino-1-(2'-hydroxyethyl)-pyrazole sulfate |
| E15 | 2,5-diaminotoluene sulfate |

TABLE 3

Direct Dyes

| | |
|---|---|
| D1 | 2,6-diamino-3-((pyridine-3-yl)azo)pyridine |
| D2 | 6-chloro-2-ethylamino-4-nitrophenol |
| D3 | 2-amino-6-chloro-4-nitrophenol |

TABLE 4

Coupling Substances

| | |
|---|---|
| K11 | 1,3-diaminobenzene |
| K12 | 2-amino-4-(2'-hydroxyethyl)amino-anisole sulfate |
| K13 | 1,3-diamino-4-(2'-hydroxyethoxy)benzene sulfate |
| K14 | 2,4-diamino-5-fluoro-toluene sulfate |
| K15 | 3-amino-2-methylamino-6-methoxy-pyridine |
| K16 | 3,5-diamino-2,6-dimethoxy-pyridine dihydrochloride |

TABLE 4-continued

Coupling Substances

| | |
|---|---|
| K17 | 2,4-diamino-5-ethoxy-toluene sulfate |
| K18 | N-(3-dimethylamino)phenylurea |
| K19 | 1,3-bis(2,4-diaminophenoxy)propane tetrahydrochloride |
| K21 | 3-amino-phenol |
| K22 | 5-amino-2-methyl-phenol |
| K23 | 3-amino-2-chloro-6-methyl-phenol |
| K24 | 5-amino-4-fluoro-2-methyl-phenol sulfate |
| K25 | 1-naphthol |
| K26 | 1-acetoxy-2-methyl-naphthalene |
| K31 | 1,3-dihydroxy-benzene |
| K32 | 2-methyl-1,3-dihydroxy-benzene |
| K33 | 1-chloro-2,4-dihydroxy-benzene |
| K34 | 4-(2'-hydroxyethyl)amino-1,2-methylenedioxybenzene hydrochloride |
| K35 | 3,4-methylenedioxy-phenol |
| K36 | 2-amino-5-methyl-phenol |

TABLE 5

Hair-Dyeing Agents

Example No.

| Dye | 17 | 18 | 19 | 20 | 21 | 22 | 23 | 24 | 25 | 26 | 27 | 28 | 29 | 30 | 31 |
|---|---|---|---|---|---|---|---|---|---|---|---|---|---|---|---|
| | (amount of dye in grams) | | | | | | | | | | | | | | |
| E1 | 0.25 | 0.20 | 0.20 | 0.20 | 0.35 | 0.25 | 0.30 | 0.10 | 0.10 | 0.15 | | | | | |
| E2 | | | | | | | | | | | 0.25 | 0.20 | 0.20 | 0.20 | 0.35 |
| E8 | | | | | | | | 0.15 | | | | | | | |
| E9 | | | | | | | | | 0.15 | | | | | | |
| E10 | 0.30 | | 0.30 | | | | | | | | 0.30 | | | | |
| E11 | | 0.30 | | | | | | | | | | 0.30 | | | |
| E12 | | | 0.30 | | | | | | | | | | 0.30 | | |
| E14 | | | | 0.30 | | | | | | | | | | 0.30 | |
| E15 | | | | | | | | | | 0.15 | | | | | |
| K12 | | | | | | | | 0.10 | | | | | | | |
| K13 | | | | | 0.09 | 0.09 | | | | | | | | | 0.09 |
| K31 | 0.18 | | | 0.20 | 0.20 | | | 0.15 | 0.20 | 0.10 | 0.18 | | | 0.20 | 0.20 |
| K32 | | 0.22 | | | | 0.20 | | 0.10 | | 0.10 | | 0.22 | | | |
| K33 | | | 0.20 | | | | 0.20 | | | | | | 0.20 | | |
| K21 | | | | | 0.05 | | | | | | | | | | 0.05 |
| K22 | | | | | | 0.05 | | | | | | | | | |
| K23 | | | | | | | 0.05 | 0.10 | 0.10 | 0.10 | | | | | |
| K25 | 0.30 | 0.30 | | 0.30 | | | | | | | 0.30 | 0.30 | | 0.30 | |
| K26 | | | 0.35 | | | | | | | | | | 0.35 | | |
| Dyeing Result | reddish brown | reddish brown | reddish brown | reddish brown | blond | blond | blond | blond | blond | blond | reddish brown | reddish brown | reddish brown | reddish brown | blond |

Example No.

| Dye | 32 | 33 | 34 | 35 | 36 | 37 | 38 | 39 | 40 | 41 | 42 | 43 | 44 | 45 | 46 | 47 |
|---|---|---|---|---|---|---|---|---|---|---|---|---|---|---|---|---|
| | (amount of dye in grams) | | | | | | | | | | | | | | | |
| E2 | 0.25 | 0.30 | 0.10 | 0.10 | 0.15 | | | | | | | | | | | |
| E3 | | | | | | 0.25 | 0.20 | 0.20 | 0.20 | 0.35 | 0.25 | 0.30 | 0.10 | 0.10 | 0.15 | |
| E4 | | | | | | | | | | | | | | | | 0.25 |
| E8 | | | 0.15 | | | | | | | | | | 0.15 | | | |
| E9 | | | | 0.15 | | | | | | | | | | 0.15 | | |
| E10 | | | | | 0.30 | | | | | | | | | | | 0.30 |
| E11 | | | | | | 0.30 | | | | | | | | | | |
| E12 | | | | | | | 0.30 | | | | | | | | | |
| E14 | | | | | | | | 0.30 | | | | | | | | |
| E15 | | | | | 0.15 | | | | | | | | | | 0.15 | |
| K12 | | 0.10 | | | | | | | | | 0.10 | | | | | |
| K13 | 0.09 | | | | | | | | | 0.09 | 0.09 | | | | | |
| K31 | | | 0.15 | 0.20 | 0.10 | 0.18 | | | | 0.20 | 0.20 | | 0.15 | 0.20 | 0.10 | 0.18 |
| K32 | b0.20 | 0.20 | 0.10 | | 0.10 | | 0.22 | | | | | 0.20 | 0.10 | | 0.10 | |
| K33 | | | | | | | | 0.20 | | | | | | | 0.20 | |

TABLE 5-continued

Hair-Dyeing Agents

| | | | | | | | | | | | | | | | | |
|---|---|---|---|---|---|---|---|---|---|---|---|---|---|---|---|---|
| K21 | 0.05 | | | | | | | | | 0.05 | | | | | | |
| K22 | | 0.05 | | | | | | | | | 0.05 | | | | | |
| K23 | | | 0.05 | 0.10 | 0.10 | 0.10 | | | | | | 0.05 | 0.10 | 0.10 | 0.10 | |
| K25 | | | | | | 0.30 | 0.30 | | 0.30 | | | | | | | 0.30 |
| K26 | | | | | | | | 0.35 | | | | | | | | |
| Dyeing Result | blond | blond | blond | blond | blond | reddish brown | reddish brown | reddish brown | reddish brown | blond | blond | blond | blond | blond | blond | reddish brown |

| | Example No. | | | | | | | | |
|---|---|---|---|---|---|---|---|---|---|
| | 48 | 49 | 50 | 51 | 52 | 53 | 54 | 55 | 56 |
| Dye | (amount of dye in grams) | | | | | | | | |
| E4 | 0.20 | 0.20 | 0.20 | 0.35 | 0.25 | 0.30 | 0.10 | 0.10 | 0.15 |
| E8 | | | | | | | 0.15 | | |
| E9 | | | | | | | | 0.15 | |
| E11 | 0.30 | | | | | | | | |
| E12 | | 0.30 | | | | | | | |
| E14 | | | 0.30 | | | | | | |
| E15 | | | | | | | | | 0.15 |
| K12 | | | | | | 0.10 | | | |
| K13 | | | | 0.09 | 0.09 | | | | |
| K31 | | | | 0.20 | 0.20 | | 0.15 | 0.20 | 0.10 |
| K32 | 0.22 | | | | | 0.20 | 0.10 | | 0.10 |
| K33 | | 0.20 | | | | 0.20 | | | |
| K21 | | | | 0.05 | | | | | |
| K22 | | | | | 0.05 | | | | |
| K23 | | | | | | | 0.05 | 0.10 | 0.10 |
| K25 | 0.30 | | 0.30 | | | | | | |
| K26 | | 0.35 | | | | | | | |
| Dyeing Result | reddish brown | reddish brown | reddish brown | blond | blond | blond | blond | blond | blond |

TABLE 6

Hair Dyeing Agents

| | Example No. | | | | | | | | | | | |
|---|---|---|---|---|---|---|---|---|---|---|---|---|
| | 57 | 58 | 59 | 60 | 61 | 62 | 63 | 64 | 65 | 66 | 67 | 68 |
| Dye | (amount of dye in grams) | | | | | | | | | | | |
| E1 | 1.80 | 1.80 | 1.80 | 0.70 | 0.70 | 0.70 | | | | | | |
| E2 | | | | | | | 2.0 | 2.0 | 2.0 | 0.8 | 0.8 | 0.8 |
| K12 | | | 0.10 | 0.10 | 0.10 | | | | 0.10 | 0.10 | 0.10 | |
| K13 | 1.10 | 1.10 | 1.10 | | | | 1.10 | 1.10 | 1.10 | | | |
| K31 | 1.10 | 1.10 | 1.10 | 0.40 | 0.40 | 0.40 | 1.10 | 1.10 | 1.10 | 0.40 | 0.40 | 0.40 |
| K23 | | 0.05 | 0.10 | 0.10 | 0.10 | | | 0.05 | 0.10 | 0.10 | 0.10 | |
| D2 | | | 0.10 | 0.10 | 0.10 | | | | 0.10 | 0.10 | 0.10 | |
| Dyeing Result | black | black | black | brown | brown | brown | black | black | black | brown | brown | brown |

| | Example No. | | | | | | | | | | | |
|---|---|---|---|---|---|---|---|---|---|---|---|---|
| | 69 | 70 | 71 | 72 | 73 | 74 | 75 | 76 | 77 | 78 | 79 | 80 |
| Dye | (amount of dye in grams) | | | | | | | | | | | |
| E3 | 2.0 | 2.0 | 2.0 | 0.8 | 0.80 | 0.80 | | | | | | |
| E4 | | | | | | | 1.9 | 1.9 | 1.9 | 0.7 | 0.75 | 0.75 |
| K12 | | | 0.10 | 0.10 | 0.10 | | | | 0.10 | 0.10 | 0.10 | |
| K13 | 1.10 | 1.10 | 1.10 | | | | 1.10 | 1.10 | 1.10 | | | |
| K31 | 1.10 | 1.10 | 1.10 | 0.40 | 0.40 | 0.40 | 1.10 | 1.10 | 1.10 | 0.40 | 0.40 | 0.40 |
| K23 | | 0.05 | 0.10 | 0.10 | 0.10 | | | 0.05 | 0.10 | 0.10 | 0.10 | |
| D2 | | | 0.10 | 0.10 | 0.10 | | | | 0.10 | 0.10 | 0.10 | |
| Dyeing Result | black | black | black | brown | brown | brown | black | black | black | brown | brown | brown |

What is claimed is:

1. A N-heteroarylmethyl-p-phenylenediamine derivative selected from the group consisting of N-thiophene-3-ylmethyl-1,4-diaminobenzene, N-furan-3-ylmethyl-1,4-diaminobenzene, N-(1H-imidazole-2-ylmethyl)-1,4-diaminobenzene, N-(1H-pyrrole-2-ylmethyl)-1,4-diaminobenzene and N-thiophene-2-ylmethyl-1,4-diaminobenzene, or a physiologically tolerated salt thereof.

2. An agent for oxidative dyeing of keratin fibers, said agent comprising at least one developing substance and at least one coupling substance, wherein said at least one developing substance is selected from the group consisting of N-thiophene-3-ylmethyl-1,4-diaminobenzene, N-furan-3-ylmethyl-1,4-diaminobenzene, N-(1H-imidazole-2-yl-methyl)-1,4-diaminobenzene, N-(1H-pyrrole-2-ylmethyl)-1,4-diaminobenzene and N-thiophene-2-ylmethyl-1,4-diaminobenzene, or a physiologically tolerated salt thereof.

3. The agent of claim 2, containing from 0.005 to 20 percent by weight of said at least one developing substance.

4. The agent of claim 2, containing from 0.005 to 20 percent by weight of said at least one developing substance and from 0.005 to 20 percent by weight of said at least one coupling substance.

5. The agent of claim 2, containing from 0.1 to 5 percent by weight of said at least one developing substance and from 0.1 to 5 percent by weight of said at least one coupling substance.

6. The agent of claim 2, wherein said at least one coupling substance is selected from the group consisting of 2,6-diamino-pyridine, 2-amino-4-[(2-hydroxyethyl)-amino]-anisole, 2,4-diamino-1-fluoro-5-methylbenzene, 2,4-diamino-1-methoxy-5-methylbenzene, 2,4-diamino-1-ethoxy-5-methylbenzene, 2,4-diamino-1-(2-hydroxyethoxy)-5-methylbenzene, 2,4-di-[(2-hydroxyethyl)amino]-1,5-dimethoxybenzene, 2,3-diamino-6-methoxypyridine, 3-amino-6-methoxy-2-(methylamino)-pyridine, 2,6-diamino-3,5-dimethoxypyridine, 3,5-diamino-2,6-dimethoxypyridine, 1,3-diaminobenzene, 2,4-diamino-1-(2-hydroxyethoxy)benzene, 2,4-diamino-1,5-di(2-hydroxyethoxy)-benzene, 1-(2-amino-ethoxy)-2,4-diaminobenzene, 2-amino-1-(2-hydroxyethoxy)-4-methylaminobenzene, 2,4-diaminophenoxyacetic acid, 3-[di(2-hydroxyethyl)amino]-aniline, 4-amino-2-di-[(2-hydroxyethyl)amino]-1-ethoxybenzene, 5-methyl-2-(1-methylethyl)-phenol, 3-[(2-hydroxyethyl)amino]-aniline, 3-[(2-aminoethyl)amino]-aniline, 1,3-di-(2,4-diamino-phenoxy)-propane, di-(2,4-diamino-phenoxy)-methane, 1,3-diamino-2,4-dimethoxybenzene, 2,6-bis-(2-hydroxyethyl)amino-toluene, 4-hydroxyindole, 3-dimethylamino-phenol, 3-diethylamino-phenol, 5-amino-2-methylphenol, 5-amino-4-fluoro-2-methyl-phenol, 5-amino-4-methoxy-2-methylphenol, 5-amino-4-ethoxy-2-methylphenol, 3-amino-2,4-dichlorophenol, 5-amino-2,4-dichlorophenol, 3-amino-2-methyl-phenol, 3-amino-2-chloro-6-methylphenol, 3-aminophenol, 2-[(3-hydroxyphenyl)-amino]acetamide, 5-[(2-hydroxyethyl)amino]-2-methylphenol, 3-[(2-hydroxyethyl)amino]-phenol, 3-[(2-methoxyethyl)amino]-phenol, 5-amino-2-ethylphenol, 2-(4-amino-2-hydroxyphenoxy)-ethanol, 5-[(3-hydroxypropyl)amino]-2-methyl-phenol, 3-[(2,3-dihydroxypropyl)-amino]-2-methylphenol, 3-[(2-hydroxyethyl)amino]-2-methylphenol, 2-amino-3-hydroxy-pyridine, 5-amino-4-chloro-2-methylphenol, 1-naphthol, 1,5-dihydroxynaphthalene, 1,7-dihydroxynaphthalene, 2,3-dihydroxynaphthalene, 2,7-dihydroxynaphthalene, 2-methyl-1-naphthol acetate, 1,3-dihydroxybenzene, 1-chloro-2,4-dihydroxybenzene, 2-chloro-1,3-dihydroxybenzene, 1,2-dichloro-3,5-dihydroxy-4-methylbenzene, 1,5-dichloro-2,4-dihydroxybenzene, 1,3-dihydroxy-2-methylbenzene, 3,4-methylene-dioxyphenol, 3,4-methylenedioxyaniline, 5-[(2-hydroxyethyl)amino]-1,3-benzodioxole, 6-bromo-1-hydroxy-3,4-methylenedioxy-benzene, 3,4-diaminobenzoic acid, 3,4-dihydro-6-hydroxy-1,4(2H)-benzoxazine, 6-amino-3,4-dihydro-1,4(2H)-benzoxazine, 3-methyl-1-phenyl-5-pyrazolone, 5,6-dihydroxyindole, 5,6-dihydroxyindoline, 5-hydroxyindole, 6-hydroxyindole, 7-hydroxyindole and 2,3-indolinedione.

7. The agent of claim 2, further comprising at least one direct dye.

8. The agent of claim 2, consisting of a hair-dyeing agent.

* * * * *